US00PP23862P3

(12) United States Plant Patent
Nystrom

(10) Patent No.: US PP23,862 P3
(45) Date of Patent: Sep. 3, 2013

(54) APPLE TREE, 'CN B60'

(50) Latin Name: *Malus domestica*
Varietal Denomination: CN B60

(76) Inventor: Charles Nystrom, Worthington, MN (US)

( * ) Notice: Subject to any disclaimer, the term of this patent is extended or adjusted under 35 U.S.C. 154(b) by 359 days.

(21) Appl. No.: 13/065,209

(22) Filed: Mar. 15, 2011

(65) Prior Publication Data

US 2012/0240295 P1 Sep. 20, 2012

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

PUBLICATIONS

Lehnert, Richard "DS 22 planned for this fall." Good Fruit Grower, Jun. 2012.*

* cited by examiner

*Primary Examiner* — Wendy C Haas
(74) *Attorney, Agent, or Firm* — Paine Hamblen, LLP

(57) ABSTRACT

A new and distinct variety of apple tree ('*Malus Domestica*') and which has been denominated varietally as 'CN B60' and which produces an attractively colored apple which is mature for harvesting and shipment approximately September 19 under the ecological conditions prevailing near Ephrata, Wash.

4 Drawing Sheets

Latin name: *Malus domestica.*
Varietal denomination: 'CN B60'.

BACKGROUND OF THE NEW VARIETY

The present invention relates to a new, novel, and distinct variety of apple tree *Malus domestica* and which has been denominated varietally, hereinafter, as 'CN B60'.

ORIGIN

The present variety of apple tree resulted from an ongoing program of fruit breeding. In this regard, seeds from the fruit produced by an open pollinated 'Honeycrisp' apple trees [U.S. Plant Pat. No. 7,197] were collected following the 1993 growing season from trees which were then growing in my orchard which is located in Worthington, Minn. This particular orchard is located in USDA hardiness zone 4B. Thereafter, the seeds were planted in 1994 and successful seedlings were cultivated and observed until the 2004 growing season. At that time, the new, promising variety 'CN B60' was identified and selected for further observation and for asexual reproduction. Second generation trees were made by removing budwood from the new variety 'CN B60' and grafting it onto EMLA 9 rootstock [unpatented]. These second generation trees were then planted in a commercial orchard which is located near Ephrata, Wash. These second generation trees have been continually observed since that time and the fruit from the second generation trees were compared and contrasted, in 2010, with the fruit produced from the original chance seedlings 'CN B60'. It was confirmed at that time that the fruit, and other tree characteristics of the original tree appear to be established, and were transmitted through in this successful asexual propagation.

SUMMARY OF THE NEW VARIETY

'CN B60' is a new and distinct variety of apple tree, which is distinguishable from its maternal parent the 'Honeycrisp' apple tree, (U.S. Plant Pat. No. 7,197) and which is the closest variety thereto by producing a fruit which has a round, flatter shape; a later harvesting date; a higher flesh pressure; a higher sugar content; a slightly lower juice pH; and a higher titratable acid [TA] content than that found in the fruit produced by its maternal parent 'Honeycrisp' (U.S. Plant Pat. No. 7,197). In addition, the new variety of apple tree is further distinguished from its maternal parent 'Honeycrisp' by its fruit skin appearance and further its flesh resists browning after being cut and exposed to the ambient atmosphere. The present variety also does not develop a bitter pit at harvest time, nor following six months under common refrigerated storage conditions.

BRIEF DESCRIPTION OF THE DRAWINGS

The accompanying drawings, which are provided, are color photographs of the new apple tree variety.

Figure 1:
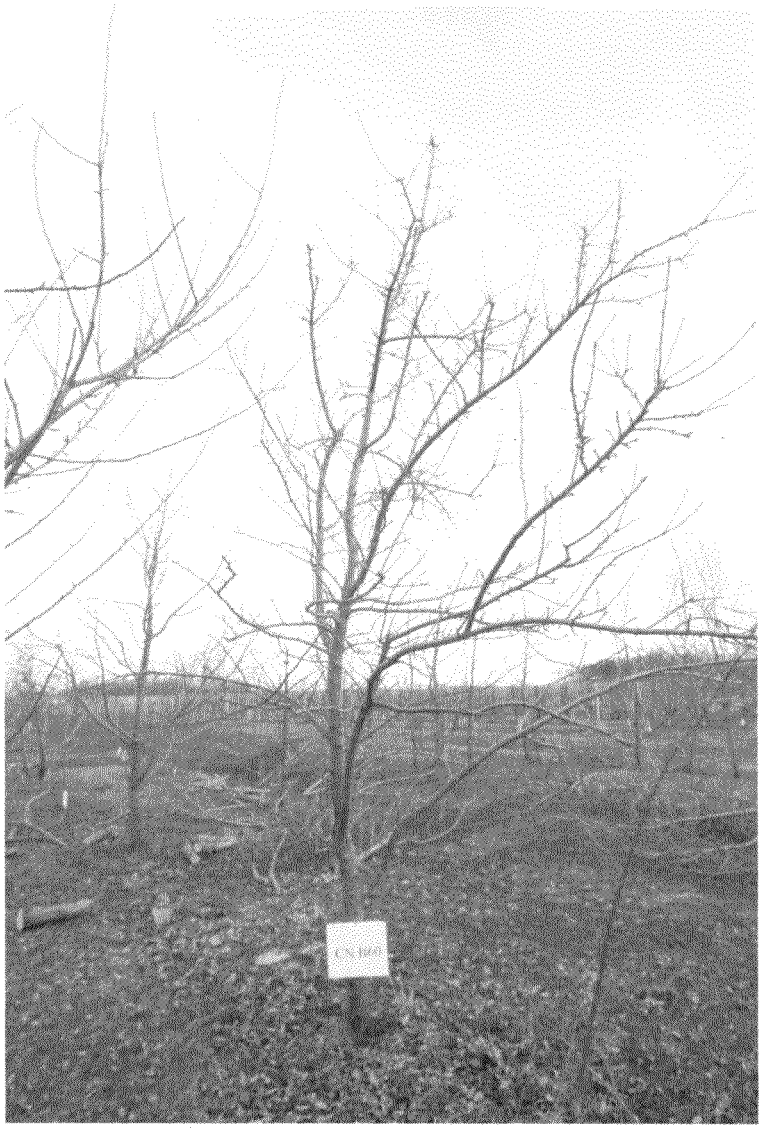
FIG. 1 depicts the original, dormant 'CN B60' mother tree as currently growing in the orchard of origin which is located in Minnesota.
Figure 2:
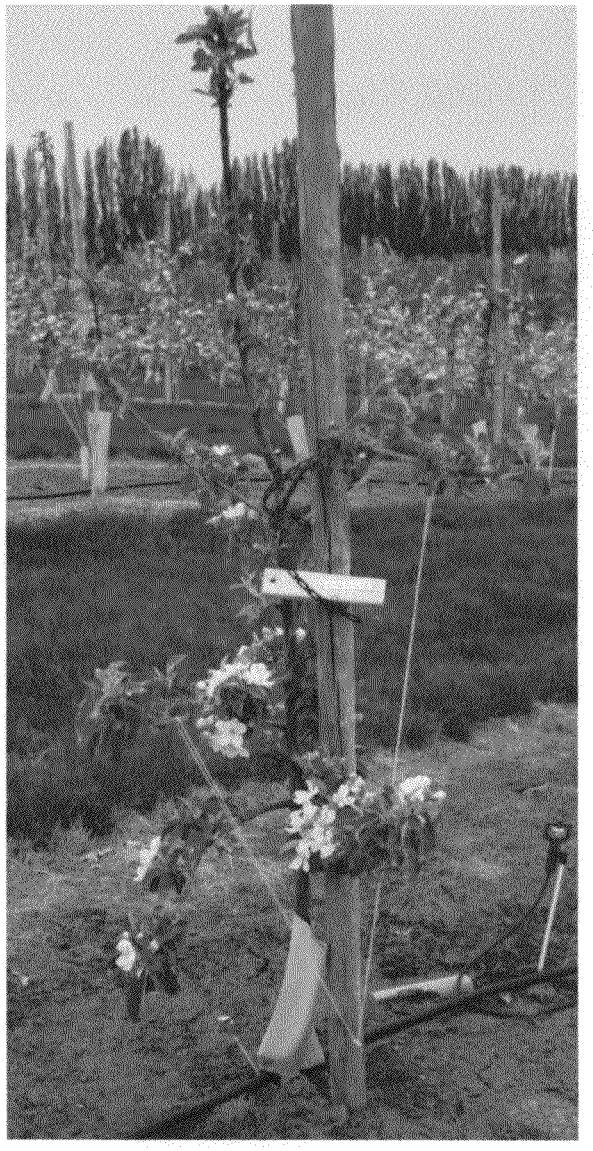
FIG. 2 is a second generation 'CN B60' apple tree as seen at full bloom.
Figure 3:
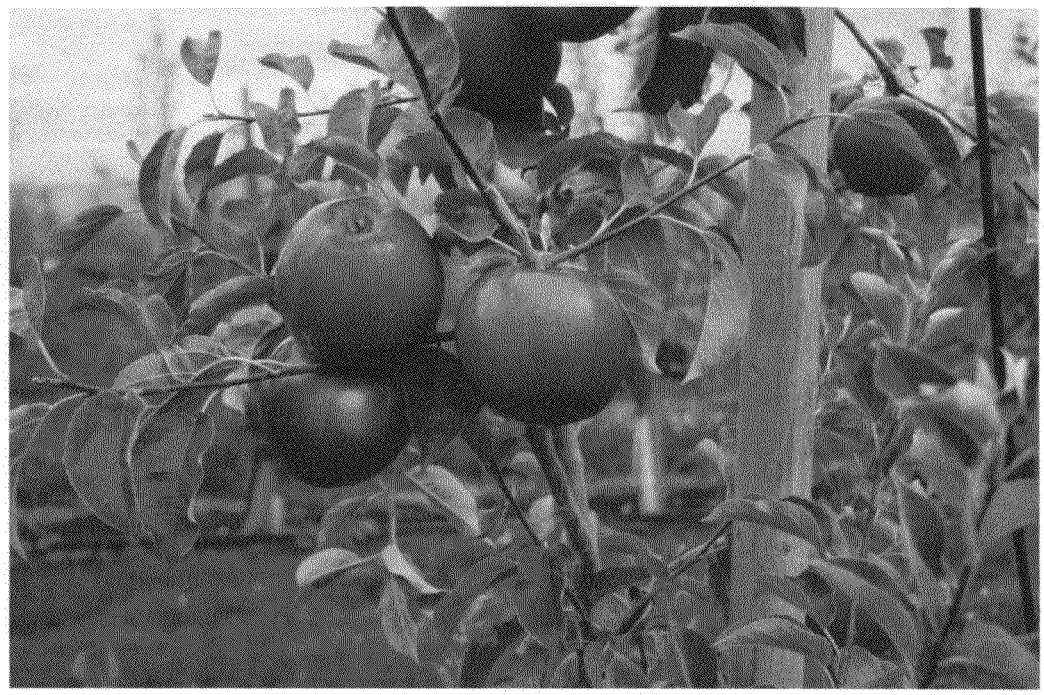
FIG. 3 depicts the fruiting characteristics of a second generation 'CN B60' apple tree at full harvest maturity.
Figure 4:
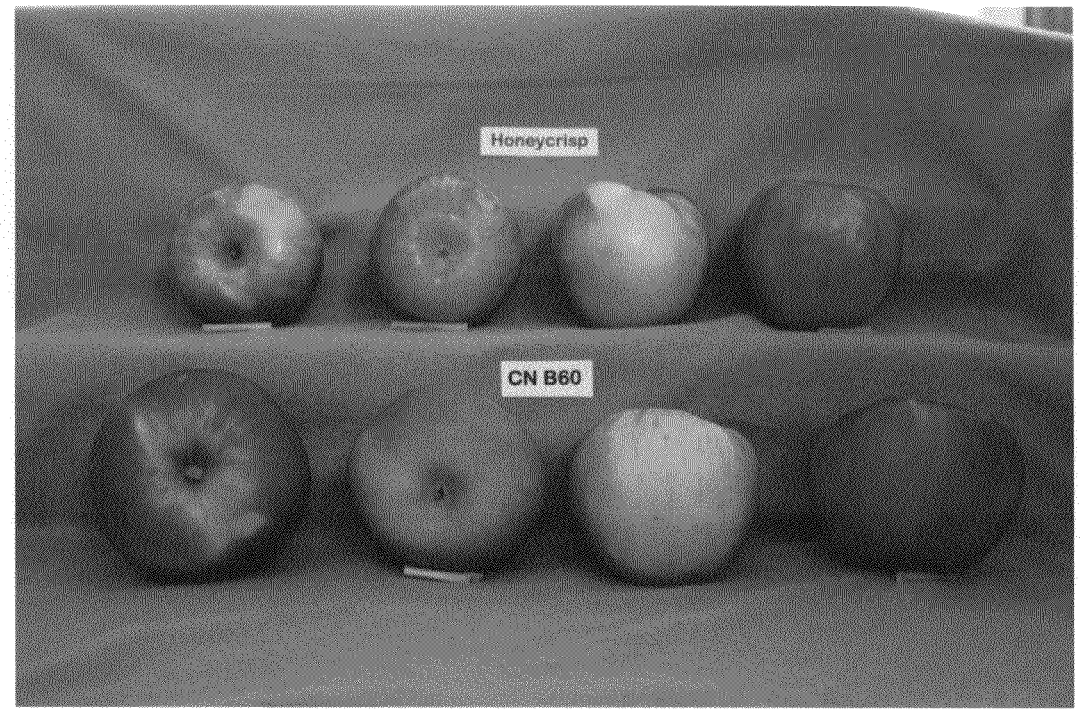
FIG. 4 is a photograph showing the fruit produced by the 'CN B60' apple tree as compared to the fruit produced by the 'Honeycrisp' apple tree [U.S. Plant Pat. No. 7,197] at full harvest maturity.

The colors in these photographs are as nearly true as is reasonably possible in a color representation of this type. Due to chemical development, processing, and printing, the leaves and fruit depicted in these photographs may, or may not be accurate when compared to the actual specimen. For this reason, future color references should be made to the color plates [Royal Horticultural Society] and the color descriptions as provided hereinafter.

NOT A COMMERCIAL WARRANTY

The following detailed description has been prepared to solely comply with the provisions of 35 U.S.C. § 112, and does not constitute a commercial warrant, (either expressed or implied), that the present variety will, in the future, display the botanical, pomological or other characteristics as set forth, hereinafter. Therefore, this disclosure may not be relied upon to support any future legal claims, including, but not limited to, breach of warranty of merchantability, or fitness for any particular purpose, or non-infringement, which is directed, in whole, or part, to the present new variety.

DETAILED DESCRIPTION

Referring more specifically to the pomological details of this new and distinct variety of apple tree, the following has been observed on second generation trees that are in their third leaf under the ecological conditions prevailing at a commercial orchard which is located near Ephrata, Wash. All major color code designations are by reference to The R.H.S. Colour Chart (Fourth Edition) and which is provided by The Royal Horticultural Society of Great Britain. Common color names are also occasionally used.

TREE

*Size.*—Generally. Considered average as compared to other common commercial apple cultivars ripening during the same season of maturity. The present tree is growing in a central leader type cultivation arrangement. As a general matter the second generation trees display moderately heavy spur development in 2010 and are otherwise considered precocious.
*Vigor.*—Considered moderate and occasionally on the light side.
*Tree shape.*—Generally considered upright spreading.
*Tree height.*—About 6.5 feet.
*Crown width.*—About 4 feet.
*Hardiness.*—Consider hardy for USDA Zone 6(a).
*Fruit productivity.*—Considered high in relative comparison to other common varieties.

TRUNK

*Size.*—Diameter. — About 20 cm when measured at a distance of about 28.7 mm above the graft union.
*Bark texture.*—Generally — Considered glabrous and displaying some netting.
*Bark color.*—Gray-brown (RHS N199 C).
*Bark lenticels.*—Generally — Present, and moderate in number. Generally, 15 lenticels will be found in a 4 square centimeter area.
*Lenticels.*—Shape — Oval.
*Lenticels.*—Width — About 1 mm.
*Lenticels.*—Length — About 2.4 mm.
*Lenticels.*—Color — Orange-white (RHS 159 A).

BRANCHES

*First year branches.*—Diameter — When measured at the midpoint of growth, the first year branches have a diameter of about 4.2 to about 6.7 mm.
*First year branches.*—Length — Variable from about 36.5 to about 48 mm.
*First year branches.*—Color — Gray-orange, (RHS Group 177 A).
*First year branches.*—Lenticels — Considered numerous. The branches typically have about 13 lenticels per square cm of surface area.
*Lenticels.*—Shape — Oval.
*Lenticels.*—Length — About 0.9 mm.
*Lenticels.*—Width — About 0.5 mm.
*Lenticels.*—Color — White (RHS 155 D).
*First year branch.*—Pubescence — Present, and considered light to moderate in abundance. Branch pubescence ranges in size from about 1 to 1.8 mm and about 0.3 mm in width.
*Branch pubescence.*—Color — White. This color is not distinctive of the variety.
*First year branch.*—Internodes — These are variable in size ranging from about 3 cm to about 4 cm.

TWO YEAR OLD FRUITING BRANCHES

*Diameter.*—At the midpoint of growth, these branches are about 9.9 mm to about 11.5 mm.
*Two year old fruiting branch spur development.*—Generally considered heavy.
*Spur.*—Length — About 10 mm to about 21.9 mm.
*Spur development.*—Bud Size — The bud diameter ranges from about 2.63 mm to about 4.19 mm.
*Bud length.*—About 5.75 mm to about 8.42 mm.
*Bud color.*—Gray-Brown (RHS N 199 B).
*First year branches.*—Lenticels — Numerous lenticels are found and average about 16 lenticels per square cm of surface area.
*Lenticels.*—Shape — Generally round and being about 0.2 to about 0.5 mm in diameter. A few elongated lenticels may be found. These elongated lenticels have a width of about 0.2 to 0.5 mm and a length of about 1 to about 2 mm.
*Lenticels.*—Color — White (RHS 155 B).
*Two year old fruiting branches.*—Bark Color — Gray-brown (RHS N 199 B).
*Scaffold branches.*—Size — About 11.3 to 14.2 mm in diameter when measured at a distance of about 10 cm from the trunk.
*Crotch angle.*—As presently trained, the new tree displays a moderate to flat crotch angle ranging from about 70° to about 90° from the vertical. This characteristic is not distinctive of the present variety, however.
*Scaffold branches.*—Color — Gray-brown (RHS N 199 A).
*Scaffold branches.*—Lenticels — Numerous, and typically averaging about 13 lenticels per square cm of surface area.
*Lenticels.*—Shape — Generally oval, though occasionally some round lenticels may be found.
*Lenticels.*—Size — About 0.5 to about 1 mm in diameter. Oval lenticels have a width of about 0.5 to about 0.75 mm, and a length of about 0.5 to about 1 mm.
*Lenticels.*—Color — Orange-white (RHS 159 C).

LEAVES

*Leaf shape.*—Generally — Considered broadly acute and upwardly folded.

*Leaf texture.*—Dorsal Surface — Considered leathery and slightly undulating.
*Leaf texture.*—Ventral Surface — Considered glabrous.
*Leaf sheen.*—The dorsal surface has a high sheen in relative comparison to the ventral surface.
*Leaf pubescence.*—Generally speaking it is present on the ventral surface only, and covers nearly the entire surface, thereof. The leaf pubescence is considered moderately fine.
*Leaf pubescence.*—Color — Gray-white (RHS 156A).
*Leaf length.*—Variable from about 80.3 mm to 101.5 mm.
*Leaf width.*—About 51.9 mm to about 71.4 mm.
*Marginal form.*—Considered bi-serrate.
*Leaf tip.*—Shape — Acuminate.
*Leaf base.*—Shape — Generally considered rounded.
*Leaf stipules.*—Generally — Present, and usually two stipules will be found per petiole.
*Leaf stipules.*—Length — About 5.2 to about 12.9 mm.
*Leaf stipules.*—Width — About 0.4 to about 2.1 mm.
*Leaf stipules.*—Color — The dorsal surface is considered yellow-green (RHS 147 A). The ventral surface is also a yellow-green color as best characterized by RHS 147 B.
*Leaf stipules.*—Pubescence — The leaf pubescence is present on both the dorsal and ventral surfaces thereof, and covers each of these surfaces in their entirety.
*Leaf pubescence.*—Color — Gray-white (RHS 156 A).
*Leaf blade.*—Color — The dorsal surface is considered to be yellow-green (RHS 147 A). The ventral surface has a yellow-green color which is most accurately characterized by RHS 147 B.
*Mid-vein.*—Generally — Prominent and having a considerable amount of fine pubescence on, or under, the surface of the vein.
*Mid-vein.*—Width — When measured at mid-blade it is about 1 mm to about 1.5 mm.
*Mid-vein.*—Dorsal Surface — Yellow-green (RHS 145 D).
*Mid-vein pubescence.*—Color — Gray-white (RHS 156 A).
*Petiole.*—Length — About 25.3 to 31.7 mm.
*Petiole.*—Diameter — When measured at the midpoint, it is about 1.5 mm to about 2.6 mm.
*Petiole.*—Color — Yellow-green (RHS 145 A). This color is highlighted at the basal end with a gray-red color (RHS 178 A).
*Petiole pubescence.*—Considered abundant and fine in texture over the entire length and circumference of the petiole.
*Petiole pubescence.*—Color — Gray-white (RHS 156 A).

FLOWERS

*Date of full bloom.*—In 2010 was April 29.
*Number of blooms per bud.*—4 to 6, mostly 5.
*Flower size.*—Generally — Considered medium to medium large for the species.
*Flower diameter.*—About 48 to about 53 mm.
*Petals.*—Width — About 17.7 mm.
*Petals.*—Length — About 21.8 mm.
*Petals.*—Color — White (RHS N155B). The petals further have highlights of gray-purple (RHS 186 D).
*Petal vein.*—Color — Gray-purple (RHS 186 D).
*Stamens.*—Numbers — About 21 to about 23 stamens will be found.
*Filament.*—Length — About 5 to about 10.2 mm.
*Filament.*—Color — Yellow-white (RHS 158 B).
*Anthers.*—Shape — Heart-like.
*Anthers.*—Width — About 2.1 mm.
*Anthers.*—Length — About 2.8 mm.
*Anthers.*—Color — When mature, the anthers are gray-yellow (RHS 160 B).
*Pistil.*—Length — About 13.9 to about 14.9 mm.
*Styles.*—Number — Five.
*Styles.*—Form — Fused near the base and a white pubescence is present at the union.
*Styles.*—Length — About 9.1 mm.
*Styles.*—Color — Green-yellow (RHS 1 C).
*Stigma.*—Shape — Club like.
*Stigma.*—Color — Yellow-green (RHS N 144 A)
*Sepals.*—Numbers — Five are typically found per blossom.
*Sepals.*—Form — The sepals are typically curled back toward the peduncle.
*Sepals.*—Shape — Considered deltoid with the tip having an acuminate shape.
*Sepals.*—Base — The base is truncated in shape.
*Sepals.*—Average Length — About 10.6 mm.
*Sepals.*—Width — About 4.2 mm.
*Sepals.*—Color — A white pubescence is present on both the dorsal and ventral surfaces thereof. The sepal color is yellow-green (RHS 144 A). The sepal tips are highlighted with a gray-orange color (RHS 166 A).
*Peduncle.*—Length — About 25 to about 30 mm.
*Peduncle.*—Color — Yellow-green (RHS 144 A). A considerable amount of white downiness is present over the entire surface of the peduncle. This color is not distinctive of other variety, however.

FRUIT

*Maturity when described.*—The present variety is ripe for harvesting and shipment under the ecological conditions prevailing in Ephrata, Wash., on or about September 19th. This date of harvesting is about 10 days later than the fruit produced by the 'Honeycrisp' apple tree (U.S. Plant Pat. No. 7,197) when grown under the same cultural conditions and at the same geographical location. The 'Honeycrisp' apple tree is the closest variety relative to the present new variety of apple tree.
*Fruit form.*—Generally considered uniform, and flat-round with a moderate amount of lopsidedness. The fruit is further lightly ribbed.
*Fruit size.*—Generally — Considered large for the species under normal crop loads. The fruit is normally considered to be two sizes larger than the fruit produced by the 'Honeycrisp' apple tree under similar crop loads.
*Fruit diameter.*—Equatorial Plane — About 94.9 mm.
*Fruit diameter.*—Axial Plane — About 77.2 mm.
*Fruit stem.*—Thickness — Average.
*Fruit stem.*—Length — Average, at about 28.2 mm.
*Fruit stem.*—Diameter — About 2.7 mm.
*Stem cavity.*—Width — About 34.6 to about 38.5 mm.
*Stem cavity.*—Depth — About 15.9 to about 24.8 mm.
*Stem cavity.*—Shape — Obtuse.

*Stem cavity.*—Lipping — The variety occasionally displays a weak lip.
*Basin cavity.*—Width — About 21.7 to 30.5 mm.
*Basin cavity.*—Depth — About 10.7 to about 12.7 mm.
*Basin cavity.*—Shape — Considered abrupt and not ribbed.
*Eye.*—Form — Erect and occasionally having reflexed tips.
*Eye.*—Sepal Color — Green (RHS 138 B).
*Eye.*—Sepal Texture — Downey. The downy is white (RHS 155 D).
*Fruit skin.*—Surface Texture — Considered slightly glabrous. A scant amount of bloom is present.
*Fruit skin.*—Texture — Considered tender.
*Fruit skin.*—Thickness — Considered thin to medium in thickness.
*Fruit skin.*—Appearance — Mostly blushed and occasionally having a light blotchy stripe.
*Fruit skin.*—Color — The over color is red (RHS 46 A). The under color is yellow (RHS 6 D).
*Fruit skin.*—Lenticels — Present, but considered small and smooth. The fruit skin lenticels are more numerous towards the calyx end of the fruit. On average about 3 lenticels per square cm appear at the stem end, and about 15 lenticels per square cm appear at the calyx end of the fruit.
*Fruit skin lenticels.*—Color — White (RHS N 155 D).
*Fruit skin lenticels.*—Size — Round and being about 0.2 to about 0.6 mm in diameter.
*Core.*—Position. — Generally considered distant.
*Core.*—Line Position. — Considered clasping.
*Core.*—Diameter — About 46.4 mm.
*Core.*—Length — About 24.8 mm.
*Core.*—Shape — Considered flat conical.
*Cell.*—Numbers — Five.
*Cell.*—Form — Tufted and having narrow lines that circumvent the cell walls.
*Tuft.*—Color — White (RHS N 155 C).
*Cell.*—Shape — Ovate.
*Cell.*—Length — About 18.2 mm.
*Cell.*—Width — About 12.9 mm.
*Tube.*—Shape — Cone like.
*Stamen.*—Position — Considered median.
*Axis.*—Considered abaxial and closed.
*Seed.*—Number — 1 to 2, mostly 2.
*Seed.*—Shape — Obtuse.
*Seed.*—Length — About 7.9 to about 8.9 mm.
*Seed.*—Width — About 4.9 to about 5.4 mm.
*Seed.*—Color — Gray-orange (RHS 177 B). The seed color will darken to a light brown color following the cutting of the fruit. This color is not distinctive of the variety, however.
*Flesh.*—Texture — Consider firm, crisp, melting and juicy.
*Flesh.*—Color — Green-white (RHS 157 D).
*Flesh.*—Aroma — Apple like, and moderate in intensity.
*Fruit.*—Pressure — About 17.04 lbs. This fruit pressure is greater than that produced by the fruit of the 'Honeycrisp' apple tree (U.S. Plant Patent No. 7,197) which on average has a fruit pressure of about 13.76 pounds.
*Brix.*—The present variety produces fruit having a brix of about 14.3. In comparison, the fruit of the 'Honeycrisp' apple tree has a brix which is typically about 13.8.
*pH.*—The present variety produces fruit which has a flesh which has a pH on average of about 3.41. This pH is less than the fruit produced by the 'Honeycrisp' apple tree (U.S. Plant Patent No. 7,197) and which produces fruit flesh having a pH of about 3.35.
*Titratable acid.*—The present variety produces fruit whose flesh has a titratable acid level of about 0.76 g/100 ml. In relative comparison, the fruit of the 'Honeycrisp' apple tree produces fruit having a titratable acid of about 0.66 grams per 100 ml.
*Keeping quality.*—Considered excellent. The fruit of the present variety has been kept up to six months in common refrigerated storage with no deleterious affects noted. Further the flesh of the new variety resists browning after being exposed to the ambient atmosphere. Further, the present variety does not develop a bitter pit either when hanging on the tree or after six months in refrigerated storage.
*Pollination.*—Any diploid apple tree blossoming in the same season may be used to pollinate the new apple tree variety.
*Fruit use.*—Considered a fresh desert apple.
*Disease and insect resistance.*—The present variety is considered to be susceptible to all insects and diseases found in the region of Central Washington State.

Although the new variety of apple tree possesses the described characteristics when grown under the ecological conditions prevailing near Ephrata, Wash., in the Central part of Washington state, it should be understood that variations of the usual magnitude and characteristics incident to changes in growing conditions, fertilization, pruning, pest control, frost, climatic variables, and horticultural management practices are to be expected.

Having thus described and illustrated my new variety of apple tree, what I claim is new and desire to secure by Plant Letters Patent is:

1. A new and distinct variety of apple tree, substantially as illustrated and described, and which is characterized as to novelty by producing an attractively colored apple which is mature for harvesting and shipment approximately September 19 under the ecological conditions prevailing near Ephrata, Wash.

* * * * *